United States Patent
Chen et al.

(10) Patent No.: US 11,839,516 B2
(45) Date of Patent: Dec. 12, 2023

(54) MEDICAL IMAGING EQUIPMENT AND MEDICAL IMAGING METHOD

(71) Applicant: Coretronic Corporation, Hsin-Chu (TW)

(72) Inventors: I-Han Chen, Hsin-Chu (TW); Chen Hsiang Shih, Hsin-Chu (TW); Yi-Fa Wang, Hsin-Chu (TW); Chih-Yang Tsai, Hsin-Chu (TW); Chia-Wei Huang, Hsin-Chu (TW)

(73) Assignee: Coretronic Corporation, Hsin-Chu (TW)

( * ) Notice: Subject to any disclaimer, the term of this patent is extended or adjusted under 35 U.S.C. 154(b) by 24 days.

(21) Appl. No.: 17/341,406

(22) Filed: Jun. 8, 2021

(65) Prior Publication Data
US 2021/0386504 A1    Dec. 16, 2021

(30) Foreign Application Priority Data
Jun. 12, 2020    (CN) .......................... 202010540094.7

(51) Int. Cl.
| | |
|---|---|
| G02B 27/00 | (2006.01) |
| A61B 90/00 | (2016.01) |
| H04N 5/262 | (2006.01) |
| G02B 27/01 | (2006.01) |
| H04N 23/63 | (2023.01) |
| G02B 27/10 | (2006.01) |
| H04N 23/50 | (2023.01) |

(52) U.S. Cl.
CPC ............ A61B 90/37 (2016.02); A61B 90/361 (2016.02); G02B 27/0176 (2013.01);
(Continued)

(58) Field of Classification Search
CPC . A61B 90/37; A61B 90/361; A61B 2090/365; A61B 2090/372;
(Continued)

(56) References Cited

U.S. PATENT DOCUMENTS

2009/0302219 A1* 12/2009 Johnson ................ G01J 5/0896
250/332
2015/0305824 A1   10/2015 Yu
(Continued)

FOREIGN PATENT DOCUMENTS

| CN | 104055478 | 9/2014 |
|---|---|---|
| CN | 106805934 | 6/2017 |

(Continued)

OTHER PUBLICATIONS

"Office Action of China Counterpart Application", dated Dec. 28, 2022, p. 1-p. 9.

*Primary Examiner* — Frank F Huang
(74) *Attorney, Agent, or Firm* — JCIPRNET

(57) ABSTRACT

Medical imaging equipment and a medical imaging method are provided. The medical imaging equipment includes medical equipment, a controller, and a head-mounted display. The medical equipment is configured to investigate a body portion and output a first image signal corresponding to the body portion. The first image signal has a first resolution. The controller is coupled to the medical equipment to receive the first image signal and convert the first resolution of the first image signal to a second image signal having a second resolution. The head-mounted display is coupled to the controller to display a display image of the second image signal. The head-mounted display has a direction line. When the head-mounted display faces the body portion, the display image and the body portion are located along to the direction line.

19 Claims, 5 Drawing Sheets

(52) U.S. Cl.
CPC ........... *H04N 5/2628* (2013.01); *H04N 23/63* (2023.01); *A61B 2090/365* (2016.02); *G02B 27/1073* (2013.01); *H04N 23/555* (2023.01)

(58) Field of Classification Search
CPC .............. A61B 2090/502; A61B 90/36; A61B 1/00045; A61B 1/04; A61B 1/2676; G02B 27/0176; G02B 27/1073; H04N 5/23293; H04N 5/2628; H04N 2005/2255; A61M 16/04

See application file for complete search history.

(56) References Cited

U.S. PATENT DOCUMENTS

| | | | | |
|---|---|---|---|---|
| 2016/0225192 | A1* | 8/2016 | Jones | G06F 3/012 |
| 2017/0323475 | A1* | 11/2017 | Moreton | G06T 15/20 |
| 2018/0092706 | A1* | 4/2018 | Anderson | A61B 90/50 |
| 2018/0256272 | A1* | 9/2018 | Maeda | G06F 3/013 |
| 2019/0149809 | A1* | 5/2019 | Chen | H04N 13/139 |
| | | | | 348/53 |
| 2020/0360097 | A1* | 11/2020 | DiMaio | A61B 34/35 |
| 2021/0137632 | A1* | 5/2021 | Stopp | A61B 17/00 |
| 2021/0227200 | A1* | 7/2021 | Hegyi | H04N 9/646 |

FOREIGN PATENT DOCUMENTS

| | | |
|---|---|---|
| CN | 107427216 | 12/2017 |
| JP | H07303225 | 11/1995 |
| JP | 2001104245 | 4/2001 |
| JP | 2008018015 | 1/2008 |
| JP | 2010142381 | 7/2010 |
| TW | M523426 | 6/2016 |

* cited by examiner

MEDICAL IMAGING EQUIPMENT AND MEDICAL IMAGING METHOD

CROSS-REFERENCE TO RELATED APPLICATION

This application claims the priority benefit of Chinese application serial no. 202010540094.7, filed on Jun. 12, 2020. The entirety of the above-mentioned patent application is hereby incorporated by reference herein and made a part of this specification.

BACKGROUND

Technical Field

The disclosure relates to an imaging device and a method, and particularly relates to medical imaging equipment and a medical imaging method.

Description of Related Art

In situations of infectious diseases (such as special infectious pneumonia), medical practitioners bear the brunt of exposure to highly risky, infectious environments, and it is particularly perilous when the medical practitioners perform short distance medical practices for highly infectious patients. For instance, when the condition of pneumonia in a patient worsens to the point that the patient cannot breathe spontaneously to maintain the oxygen supply required by the body, it is particularly important for medical practitioners to place an endotracheal tube (i.e., to perform intubation) for the patient.

Taking the aforementioned intubation as an example, image system auxiliaries currently adopted in hospitals or medical institutions require to be accompanied with additional screens so that medical practitioners can confirm body internal structures of patients during the intubation. Therein, images displayed on the screen are necessary in order to confirm the inside of the human body and correctness of the intubation position. Current manners of screen configuration include screens directly disposed on handheld intubation equipment and external screens.

Regarding the screens disposed on the handheld intubation equipment, of which intubation tools are held by the user, when operating the tools, the medical practitioners need to focus their sights on the screens beside the operated intubation tools. Although it is easy for the medical practitioners to get the hang of it, one disadvantage is that larger images cannot be displayed due to limitation by the screen size. If the screen size is increased, the intubation equipment will become excessively large and heavy, and inconvenient for use by the medical practitioners. In contrast, if the screen size is overly small, the field of view of the intubation image will be limited, which affects the intubation success rate for the medical practitioners.

On the other hand, regarding external screens, although the disadvantages of the abovementioned manner can be prevented by choosing a screen with a high resolution or in a larger size, however, it is necessary for the medical practitioners to hold the intubation tool, facing the patient, placing their sights on the external screen and the like at the same time, which leads to an issue of the hands and the eyes being in different directions. Once the eyes of the tool operating medical practitioners deviate from the patient, not only the relative position with respect to the patient can be easily neglected, but the difficulty is also increased in hand-eye coordination. In addition, this issue will extend the learning curve of the medical practitioners for operating such equipment. Beginners need to go through practices and practices on relative anatomical positions to gradually get on track, which is undoubtedly a nightmare in view of the urgency of intubation in emergency first aid.

Regarding the abovementioned manners, images in the first manner may be too small for the medical practitioners to clearly recognize, which affects the success rate of intubation; in addition, after applying the second manner for a long time, the medical practitioners are prone to injuries due to the hands and the eyes being in different axes, which also affects concentration during surgery.

In summary of the foregoing, a technology is worth developing which provides medical imaging equipment and a medical imaging method so that medical practitioners can have images having sufficient sizes and resolutions when operating tools, and that the sights of the medical practitioners, the image, and the patient can be located along to the same direction line.

The information disclosed in this Background section is only for enhancement of understanding of the background of the described technology and therefore it may contain information that does not form the prior art that is already known to a person of ordinary skill in the art. Further, the information disclosed in the Background section does not mean that one or more issues to be resolved by one or more embodiments of the invention was acknowledged by a person of ordinary skill in the art.

SUMMARY

Based on the above description, the disclosure proposes medical imaging equipment and a medical imaging method.

According to an embodiment, the disclosure provides medical imaging equipment including medical equipment, a controller, and a head-mounted display. The medical equipment is configured to investigate a body portion and output a first image signal corresponding to the body portion. The first image signal has a first resolution. The controller is coupled to the medical equipment to receive the first image signal and convert the first resolution of the first image signal to a second resolution of a second image signal. The head-mounted display is coupled to the controller to display a display image of the second image signal having the second resolution. The head-mounted display has a direction line. When the head-mounted display faces the body portion, the display image and the body portion are located along to the direction line.

According to an embodiment, the disclosure provides a medical imaging method adapted for a head-mounted display, medical equipment, and a controller which is coupled to the head-mounted display and the medical equipment. The medical imaging method includes the following steps. First, a body portion is investigated and a first image signal corresponding to the body portion is output by the medical equipment, in which the first image signal has a first resolution. Next, the first image signal is received and the first resolution of the first image signal is converted into a second resolution of a second image signal by the controller. Then, a display image of the second image signal having the second resolution is displayed by the head-mounted display, in which the head-mounted display has a direction line, and when the head-mounted display faces the body portion, the display image and the body portion are located along to the direction line.

Based on the above, through the medical imaging equipment and the medical imaging method of the disclosure, since the sight of the user, the display image of the head-mounted display, the patient and the like are all located along to the same direction line, the user can confirm the image of the intubation process without shaking the head between an operational tool and an external display, and concentration of the user can accordingly be enhanced, which increases the efficiency of the medical practice, and also reduces the error rate. In addition, the controller can convert various resolutions adopted by different medical equipment into the resolution adopted by the head-mounted display. Therefore, the disclosure can be applied to various medical equipment, which increases the degree of freedom of the application thereof.

Other objectives, features and advantages of the present invention will be further understood from the further technological features disclosed by the embodiments of the present invention where there are shown and described preferred embodiments of this invention, simply by way of illustration of modes best suited to carry out the invention.

BRIEF DESCRIPTION OF THE DRAWINGS

The accompanying drawings are included to provide a further understanding of the invention, and are incorporated in and constitute a part of this specification. The drawings illustrate embodiments of the invention and, together with the description, serve to explain the principles of the invention.

DESCRIPTION OF THE EMBODIMENTS

It is to be understood that other embodiment may be utilized and structural changes may be made without departing from the scope of the present invention. Also, it is to be understood that the phraseology and terminology used herein are for the purpose of description and should not be regarded as limiting. The use of "including," "comprising," or "having" and variations thereof herein is meant to encompass the items listed thereafter and equivalents thereof as well as additional items. Unless limited otherwise, the terms "connected," "coupled," and "mounted," and variations thereof herein are used broadly and encompass direct and indirect connections, couplings, and mountings.

Figure 1:
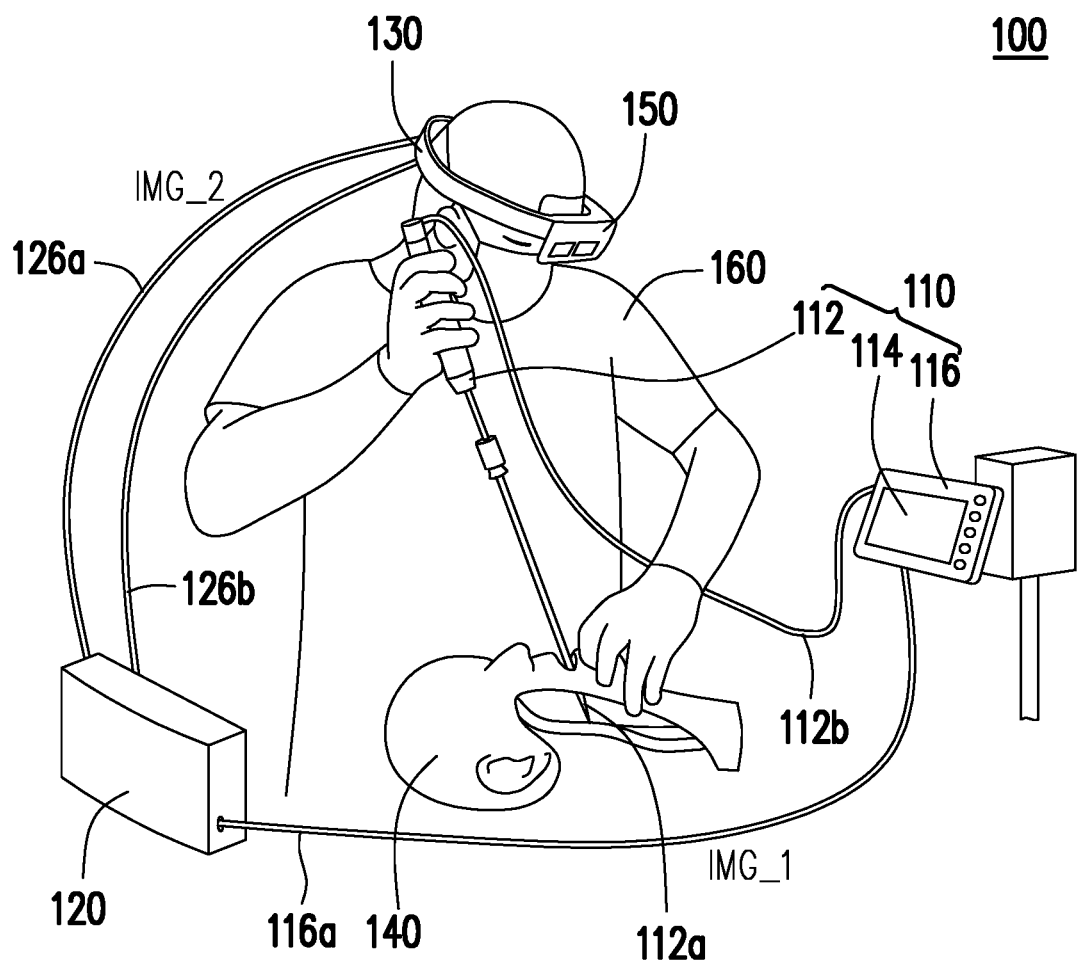
FIG. 1 is a schematic structural diagram of medical imaging equipment according to an embodiment of the disclosure.

FIG. 1 is a schematic structural diagram of medical imaging equipment according to an embodiment of the disclosure. As shown in FIG. 1, medical imaging equipment 100 includes at least medical equipment 110, a controller 120, and a head-mounted display 130. The medical equipment 110 is configured to investigate or detect a body portion of the patient 140 (e.g., a body portion 142 shown in FIG. 2) and output a first image signal IMG_1 corresponding to the body portion 142. The first image signal IMG_1 has a first resolution, such as 1920×1080. The controller 120 is coupled to the medical equipment 110 to receive the first image signal IMG_1 and convert the first resolution of the first image signal IMG_1 into a second resolution of a second image signal IMG_2. The second resolution may be 1280×720, for instance. The head-mounted display 130 is coupled to the controller 120 to display a display image of the second image signal IMG_2 having the second resolution. However, the disclosure is not limited thereto. The controller 120 can adjust the resolution of the image to be output.

Figure 2:
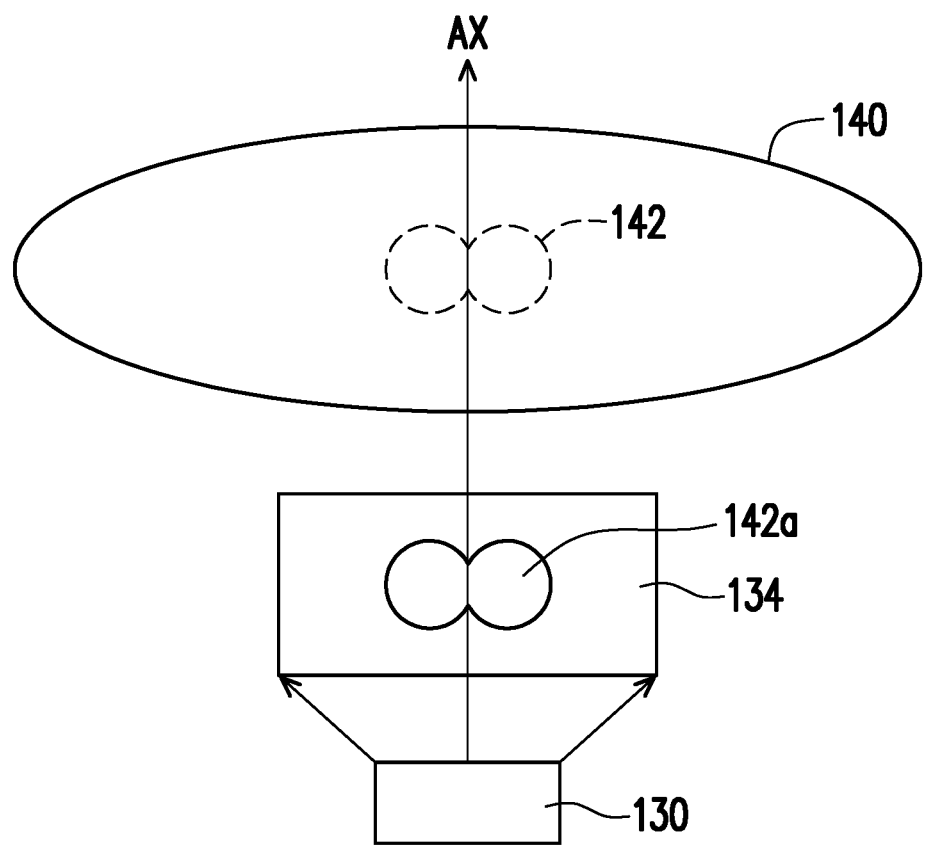
FIG. 2 is a schematic diagram of coaxial imaging of medical imaging equipment according to an embodiment of the disclosure.
Figure 4A:
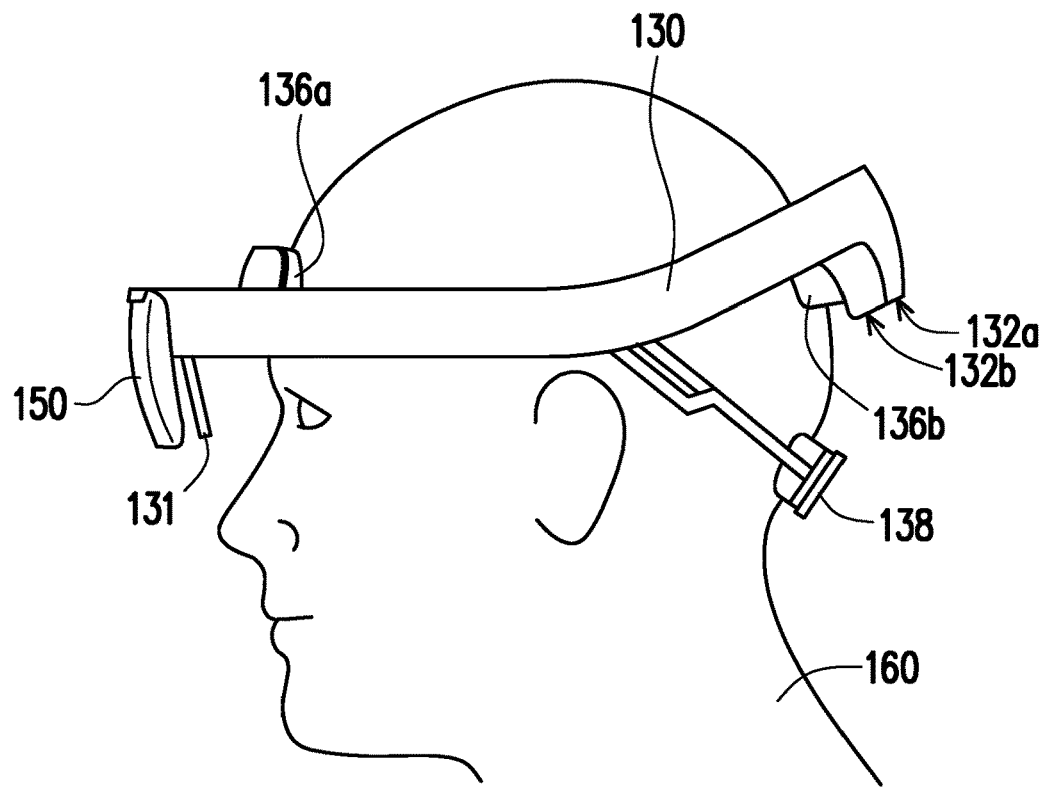
FIG. 4A illustrates a side view of the head-mounted display of FIG. 1.

FIG. 2 is a schematic diagram of coaxial imaging of medical imaging equipment according to an embodiment of the disclosure. As shown in FIG. 2, the head-mounted display 130 has a direction line AX. The direction line AX is a virtual line. When the head-mounted display 130 on the user 160 faces the body portion 142, a displayed image 134, an image capturing device 112a of an operational tool 112, and the body portion 142 of the patient 140 are located along to the direction line AX. In detail, when the medical imaging equipment in this embodiment is operated so that the head-mounted display 130 faces the body portion 142, a display of the head-mounted display 130 (such as augmented reality glasses 131, as shown in FIG. 4A), an body portion image 142a of the image 134 displayed on the display, and the actual body portion 142 of the patient 140 are all located along to the direction line AX. Therefore, according to this embodiment, when the user 160 operates the operational tool 112, the display of the head-mounted display 130 may also display the image 134 in real time. In addition, since the display, the operational tool 112, the patient 140, the body portion 142 of the patient 140, and the body portion image 142a of the image 134 are all located along to the same direction line, the user 160 can operate the operational tool 112 and compare the body portion image 142a of the patient directly through the head-mounted display 130 instead of turning or shaking the head of the user. Therefore, the user 160 can focus on surgery on the patient 140 instead of being distracted by the needs to look elsewhere at the body portion image 142a.

In an embodiment, the controller 120 and the medical equipment 110 may adopt a wired connection, such as through a signal line 116a, to thereby transmit the first image signal IMG_1 obtained by the medical equipment 110 on the patient 140 to the controller 120. In addition, the controller 120 and the head-mounted display 130 may also adopt a wired connection, such as through a signal line 126a, to thereby transmit the second image signal IMG_2 converted by the controller 120 to the head-mounted display 130.

According to an embodiment, in the medical imaging equipment 100, the medical equipment 110 may further include the operational tool 112, the image capturing device 112a, and a console 116. The operational tool 112 is configured to investigate the body portion 142 of the patient 140. The image capturing device 112a is disposed on a front end of the operational tool 112 to acquire and output the first image signal IMG_1. The console 116 has a display 114, and is configured to receive and display the first image signal IMG_1, and transmit the first image signal IMG_1 to the controller 120.

In this embodiment, a tracheal tube is adopted as an illustrative example of the operational tool 112, but the disclosure is not particularly limited to the tracheal tube when implemented. Any device which is applied so that medical practices or investigations on patient 140 are accompanied with images can serve as the operational tool 112. For instance, the operational tool 112 may as well be an endoscope, a gastroscope, a medical instrument for minimally invasive surgery, an ultrasound scanning instrument, or the like to which the configuration of the disclosure may apply.

In addition, the image capturing device 112a mounted on the front end of the operational tool 112 mainly captures images of human tissues, organs, and the like around the front end of the operational tool 112, and produces and outputs the first image signal IMG_1 when the operational tool 112 enters the body of the patient 140. The console 116 may configure the operational tool 112, receive the first image signal IMG_1 captured by the image capturing device 112a, and display the image of the first image signal IMG_1 on the display 114. In addition, the display 114 meanwhile also serves as an interface for configuring the operational tool 112.

The abovementioned image capturing device 112a may be, for instance, various image sensing devices, such as an image sensing device composed of a CCD or a CMOS, or a structure composed of a light source and a mirror. In this embodiment, the specific structure or type of the image capturing device 112a is not particularly limited, as long as image capturing can be performed on human tissues, organs, and the like around the front end of the operational tool 112. In addition, in one embodiment, the image capturing device 112a and the console 116 may adopt a wired connection, such as through a signal line 112b, to transmit the first image signal IMG_1 to the console 116. In addition, the resolution of the image capturing device 112a for a general intubation or an endoscopy may be an HD resolution, such as 1080P, or a high resolution of 4K or 8K that provides images of the body portion 142 of patient 140 at a higher resolution.

Figure 3A:
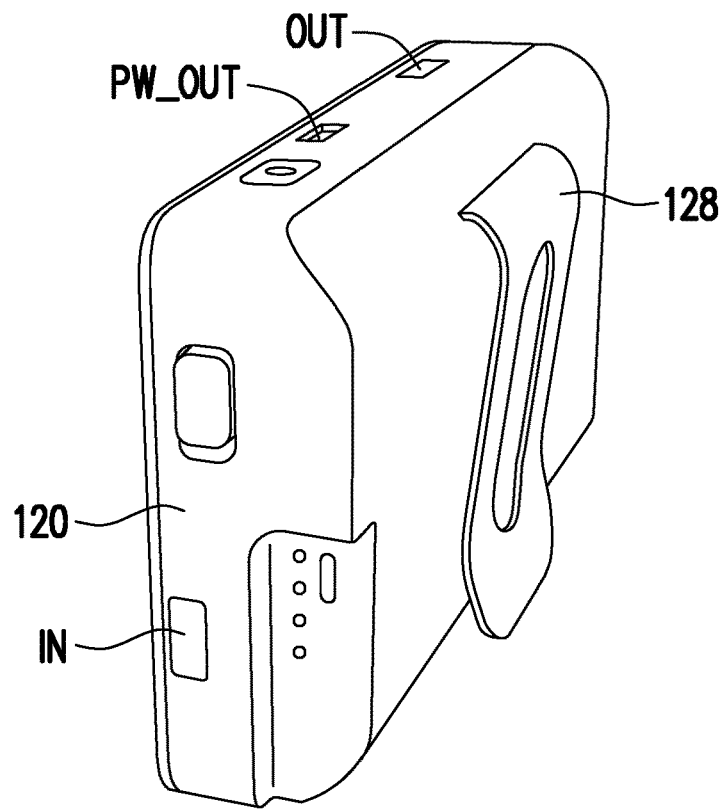
FIG. 3A is a schematic view showing the controller of FIG. 1.
Figure 3B:
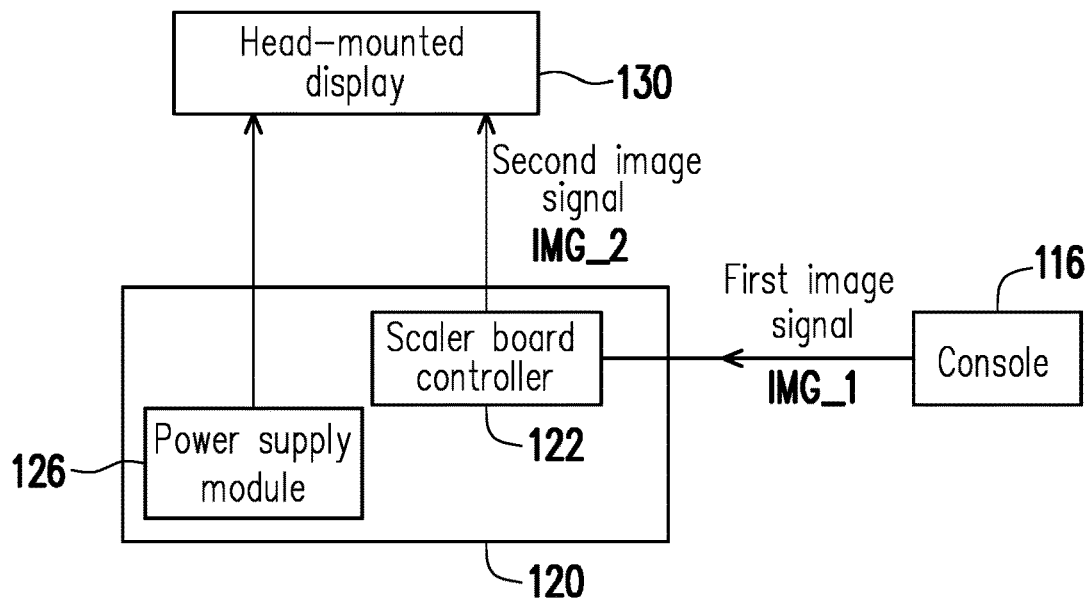
FIG. 3B is a schematic circuit block diagram of the controller of FIG. 1.

FIG. 3A is a schematic view showing the controller of FIG. 1. FIG. 3B is a schematic circuit block diagram of the controller of FIG. 1. As shown in FIG. 3A, the controller 120 may have a switch. After switched on, the controller 120 may control, for instance, the head-mounted display 130 of the medical imaging equipment 100. The controller 120 may have at least an image signal input terminal IN, an image signal output terminal OUT, and a power output terminal PW_OUT. With reference to FIG. 1, the image signal input terminal IN may be connected to the console 116 through the signal line 116a, thereby receiving the first image signal IMG_1. The signal line 116a herein may be a signal line of HDMI specifications or a signal line of other specifications. The image signal output terminal OUT may be connected to the head-mounted display 130 through the signal line 126a, thereby transmitting the second image signal IMG_2 converted from the first image signal IMG_1 to the head-mounted display 130. The signal line 126a herein may be a signal line of HDMI specifications or a signal line of other specifications. In addition, the power output terminal PW_OUT of the controller 120 is connected to a power cord 126b, and then connected to the head-mounted display 130, thereby providing the head-mounted display 130 with power required for operation.

Next, the structure of the controller 120 will be described. As shown in FIG. 3B, the controller 120 may further include a scaler board controller 122 and a power supply module 126. Only the relevant to the operation in this embodiment is illustrated in the functional blocks in the circuit block diagram shown in FIG. 3B, and the rest are omitted. People having ordinary skill in the art may appropriately add corresponding circuit blocks in order to realize the operation of the controller 120, which will not be described in detail herein.

The scaler board controller 122 may be coupled to the console 116 of the medical equipment 110 to receive the first image signal IMG_1 output by the image capturing device 112a of the operational tool 112, converts the first resolution of the first image signal IMG_1 into the second resolution, and outputs the second image signal having the second resolution. Since the resolution adopted by the head-mounted display 130 is not necessarily the same as the resolution of the first image signal IMG_1 output by the image capturing device 112a, it is likely that images cannot be displayed on the head-mounted display 130 due to a resolution difference. Therefore, the scaler board controller 122 converts the first resolution into the second resolution adopted by the head-mounted display 130 so that images can be displayed on the head-mounted display 130 normally.

In addition, the power supply module 126 is coupled to the head-mounted display 130 and supplies power to the head-mounted display 130. As shown in FIG. 3A, the power output terminal PW_OUT is connected to the power cord 126b, and then connected to the head-mounted display 130, thereby transmitting power to a system in the head-mounted display 130 for use. The power supply module 126 is, for instance, a rechargeable battery or the like. When the controller 120 is not in use, the power supply module may be charged, so that when the medical imaging equipment 100 is operated, the head-mounted display 130 can have sufficient power, to ensure that power would not fail for the head-mounted display 130 during the surgery on the patient 140.

Figure 4B:
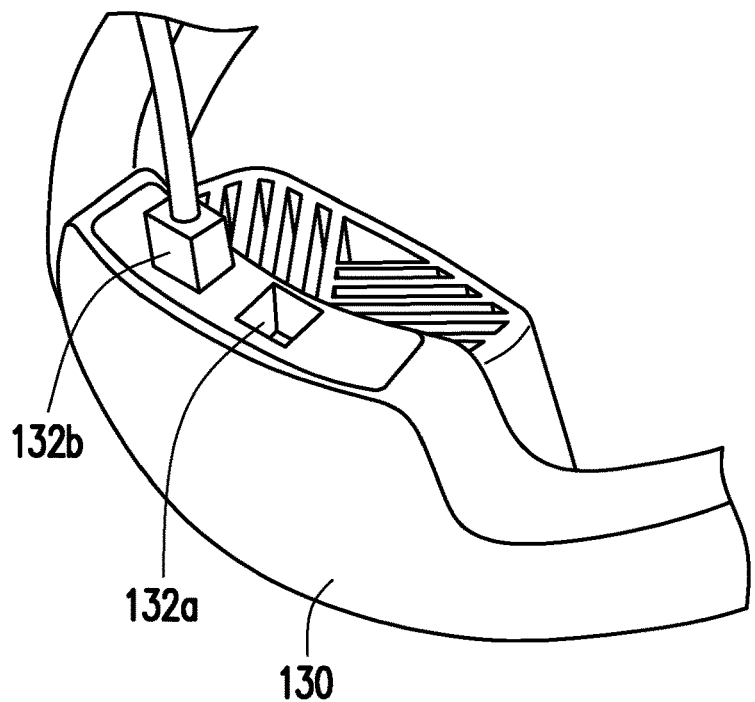
FIG. 4B illustrates a bottom view of the head-mounted display of FIG. 1.

FIG. 4A illustrates a side view of the head-mounted display of FIG. 1. FIG. 4B illustrates a bottom view of the head-mounted display of FIG. 1. As shown in FIG. 4A, the head-mounted display 130 may be provided with a forehead pad 136a and a back cushion 136b. Thereby, the head-mounted display 130 when worn on the head of the user 160 is supported, so that the head-mounted display 130 can be fixed on the head of the user 160. In addition, the head-mounted display 130 can be provided with an elastic band 138, by which the head-mounted display 130 can be further fixed according to the head shape of the user 160. The forehead pad 136a and the back cushion 136b may adopt rubber materials to provide greater wearing comfort. The elastic band 138 may be disposed on a rear side of the head-mounted display 130 to prevent influences on the user 160 performing the surgery on the patient 140.

In addition, as shown in FIG. 4B, an input port end may be disposed on the rear side (opposite side to the forehead) of a case of the head-mounted display 130, which includes an image signal input terminal 132a and a power input terminal 132b. The image signal input terminal 132a may be connected to the image signal output terminal OUT of the controller 120 through the signal line 126a (shown in FIG. 1) to receive the second image signal IMG_2. Herein, the signal line 126a may be a signal line of HDMI specifications or a signal line of other specifications. Moreover, the power input terminal 132b may be connected to the power output terminal PW_OUT of the controller 120 through the power cord 126b (shown in FIG. 1) to receive power from the power supply module 126. Furthermore, the image signal input terminal 132a, the power input terminal 132b, and the like may be disposed on the rear side of the case of the head-mounted display 130, namely, a location close to the back of the head, thereby preventing disturbance to the sight of the user 160 during operation.

As shown in FIG. 4A, the head-mounted display 130 may further include augmented reality glasses 131 as well as an optical engine (not shown). The second image signal IMG_2 output from the controller 120 is received by the optical engine and is imaged on the augmented reality glasses 131. The augmented reality glasses 131 may be composed of a waveguide, a tilt waveguide, or a prism.

According to an embodiment, a transmittance of lenses of the augmented reality glasses 131 may be between 60% and 90%. Accordingly, after wearing the head-mounted display 130, the user 160 can see, for instance, an expression of the patient 140, the actual operational tool 112 (e.g., a laryngoscope), and the image (e.g., the displayed image of the second image signal exhibited on the lenses of the augmented reality glasses 131) captured by the image capturing device 112a at the same time. In this way, since the augmented reality glasses 131 and the image capturing device 112a of the operational tool 112 are both within a fixed sight range of the user 160, namely located along to the same direction line AX as shown in FIG. 2, the user 160 can compare the image 134 captured by the operational tool 112 and operate the operational tool 112 at the same time through the head-mounted display 130. Therefore, when operating the operational tool 112, the user 160 can directly compare the image 134 captured by the operational tool 112 at the same time without shaking the head, and the user 160 can thus be more focused on performing the surgery on the patient 140, instead of being distracted by the needs to shake the head elsewhere to watch the image. Accordingly, through the coaxial architecture in this embodiment, the user 160 can perform the surgery more intensively through using the augmented reality glasses 131, which increases the accuracy of the surgery and reduces the error rate.

In addition, the head-mounted display 130 may further include a processor (not shown), which may be disposed near the input port end on the rear side of the case of the head-mounted display 130 as shown in FIG. 4B. For instance, a printed circuit board including this processor may be disposed. The processor may receive the second image signal IMG_2 and generate a drive signal to drive the optical engine. Thereby, the second image signal is displayed on the lenses of augmented reality glasses 131. In an embodiment, the optical engine may further include a light source and a light valve. The manners of configuration of the light source and the light valve are not particularly limited.

Also, according to an embodiment, the head-mounted display 130 may further include detachable goggles 150 disposed on the head-mounted display 130 and before the lenses of the augmented reality glasses 131. The detachable goggles 150 can block droplets produced from coughing by the patient 140 when being intubated, which prevents the droplets from contaminating the lenses of the augmented reality glasses 131. Therefore, even in such cases, the user 160 can clearly see a laryngoscopic image, instead of being unable to clearly see the complete laryngoscopic image due to a part of the display covered by the droplets splashed from the patient.

Moreover, the detachable goggles 150 of this embodiment may be replaced (for example, if contaminated). Therefore, the detachable goggles 150 can also reduce the chance of clinical contamination. In addition, the detachable goggles 150 may be lenses having a shading effect, such as sunglasses, which can block an external light source, change the extent to which images on the augmented reality glasses 131 can be accepted by the eyes of the user 160, and thereby enhance an image clarity of the augmented reality glasses 131.

In addition, in the foregoing description of the medical imaging equipment 100, the first image signal IMG_1 output by the medical equipment 110 is transmitted to the controller 120 through the signal line 116a, and the second image signal IMG_2 is transmitted by the controller 120 to the head-mounted display 130 through the signal line 126a. That is, the image signal transmission is performed through wired transmission. Nonetheless, at least one of receiving the first image signal IMG_1 by the controller 120 and receiving the second image signal IMG_2 by the head-mounted display 130 may as well be performed through wireless transmission. For instance, any wireless transmission technology available such as WiFi, wireless network, and the like may be adopted. In addition, the transmission of the first image signal IMG_1 between the operational tool 112 and the console 116 in the medical equipment 110 may also be performed through the various abovementioned wireless transmission methods.

In addition, as shown in FIG. 3A, the controller 120 in this embodiment may further include a clipping part 128, which may be disposed at any appropriate position on the case of the controller 120. Through the clipping part 128, the controller 120 can be stably fixed on the user 160. The clipping part 128 can be manufactured with a thin metal plate, for instance. In this way, it is likely the controller 120 does not interfere with the operation of the medical equipment 110 by the user 160.

In addition, according to an embodiment of the disclosure, the controller 120 may also be integrated into the head-mounted display 130. That is, the controller 120 and the head-mounted display 130 may be integral. For instance, the scaler board controller 122 and the power supply module 126 shown in FIG. 3B may be disposed in the head-mounted display 130. In this way, the entire medical imaging equipment 100 can be more portable.

Figure 5:
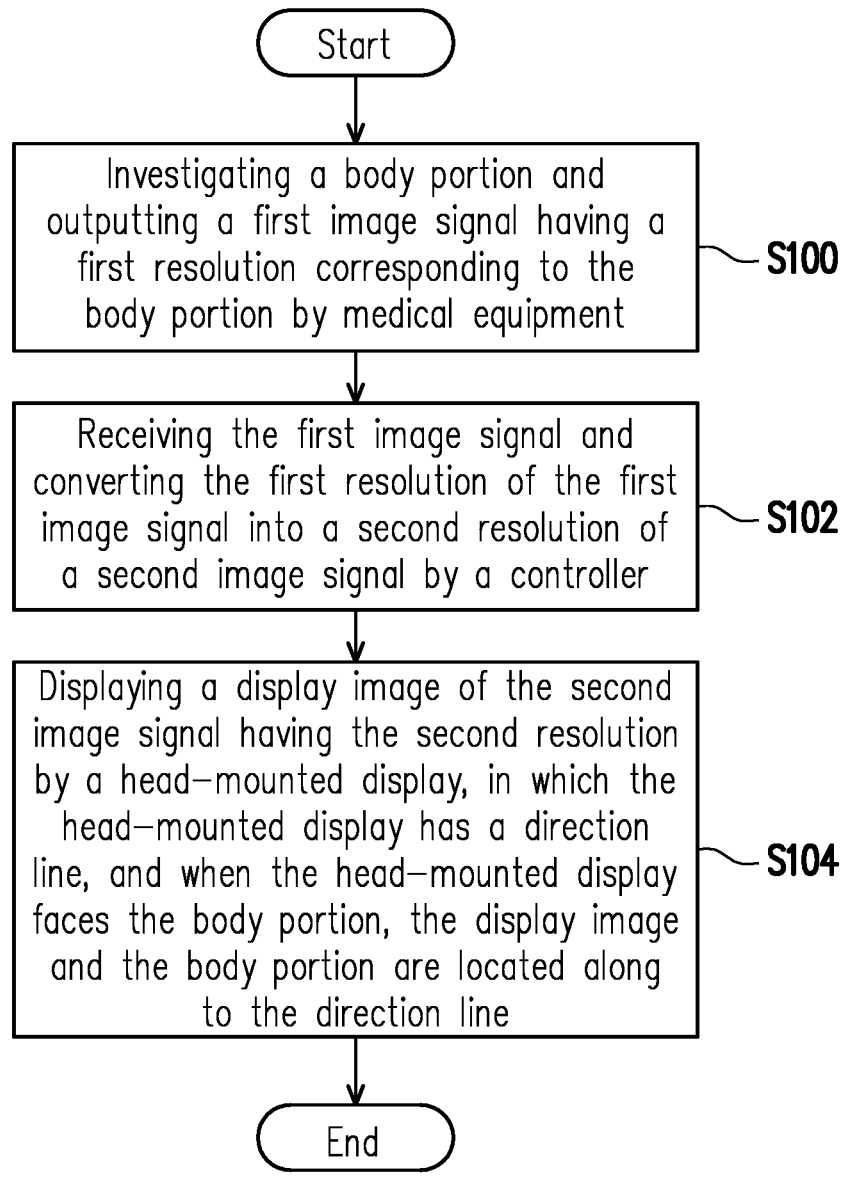
FIG. 5 is a schematic flowchart of a medical imaging method according to an embodiment of the disclosure.

FIG. 5 is a schematic flowchart of a medical imaging method according to an embodiment of the disclosure. The process of the imaging method shown in FIG. 5 may be adapted for the head-mounted display 130, the medical equipment 110, and the controller 120 coupled to the head-mounted display 130 and the medical equipment 110 as shown in FIG. 1.

As shown in FIG. 5 and FIG. 1, firstly in step S100, a body portion 142 of a patient 140 is investigated through medical equipment 110, and a first image signal IMG_1 corresponding to the body portion is output, in which the first image signal has a first resolution. For instance, an image capturing device 112a of an operational tool 112 shown in FIG. 1 may be adopted to capture and output the first image signal IMG_1.

Next, in step S102, the first image signal is received, and the first resolution of the first image signal is converted into a second resolution of a second image signal IMG_2 by a controller 120. With reference to FIG. 1, a user 160 may operate the operational tool 112 to enter the body of the patient 140 and capture an image to thereby output the first image signal IMG_1. The controller 120 may receive the first image signal IMG_1 and convert the first resolution of the first image signal IMG_1 into the second resolution adapted for displaying by a head-mounted display 130. Also, the controller 120 outputs the second image signal IMG_2 having the second resolution.

In step S104, a display image of the second image signal having the second resolution is displayed through the head-mounted display 130. The head-mounted display 130 has a direction line AX. When the head-mounted display 130 faces the body portion 142 of the patient 140, the displayed image 134 and the body portion 142 are located along to the direction line. In this way, after wearing the head-mounted display 130, the user 160 can see, for example, an expression of the patient 140, the actual operational tool 112 (e.g., a laryngoscope), and the image (e.g., the display image 134 of the second image signal exhibited on lenses of augmented reality glasses 131) captured by the image capturing device 112a at the same time.

In the above medical imaging method, such as in step S102, the controller 120 may receive the first image signal IMG_1, convert the first resolution into the second resolution, and output the second image signal IMG_2 with the second resolution through a scaler board controller 122 shown in FIG. 3B.

In addition, in the above step S100, the body portion 142 of the patient 140 may be investigated through the operational tool 112. Then, through the image capturing device 112a of FIG. 1, the first image signal IMG_1 is captured and output. Next, at a console 116, the operational tool 112 is controlled, the first image signal IMG_1 is received and displayed on a display 114 of the console 116, and the first image signal IMG_1 is transmitted to the controller 120.

In summary of the foregoing, through the medical imaging equipment and the medical imaging method in this embodiment, the augmented reality glasses of the head-mounted display are adopted to display the body portion of the patient. Therefore, the augmented reality glasses of the head-mounted display and the operational tool are both within a fixed sight range of the user, namely located along to the same direction line.

Accordingly, the user can compare the image captured by the operational tool and operate the operational tool at the same time. Therefore, when operating the operational tool, the user can directly compare the image captured by the operational tool at the same time without shaking the head, and the user can thus be more focused on performing the surgery on the patient instead of being distracted by the needs to look elsewhere at the image. Therefore, the user can perform the surgery more intensively through using the augmented reality glasses, which increases the efficiency of the medical practice and the accuracy of the surgery, and also reduces the error rate. In addition, the controller can convert various resolutions adopted by different medical equipment into the resolution adopted by the head-mounted display. Therefore, the disclosure can be applied to various medical equipment. Even if blood or droplets splash from the patient during the surgery, the adopted detachable goggles would not affect the sight of the user.

The aforementioned description of the preferred embodiments of the invention has been presented for purposes of illustration and description. It is not intended to be exhaustive or to limit the invention to the precise form or to exemplary embodiments disclosed. Accordingly, the foregoing description should be regarded as illustrative rather than restrictive. Obviously, many modifications and variations will be apparent to practitioners skilled in this art. The embodiments are chosen and described in order to best explain the principles of the invention and its best mode practical application, thereby to enable persons skilled in the art to understand the invention for various embodiments and with various modifications as are suited to the particular use or implementation accordingly. It is intended that the scope of the invention be defined by the claims appended hereto and their equivalents in which all terms are meant in their broadest reasonable sense unless otherwise indicated. Therefore, the term "the invention", "the present invention" or the like does not necessarily limit the claim scope to a specific embodiment, and the reference to particularly preferred exemplary embodiments of the invention does not imply a limitation on the invention, and no such limitation is to be inferred. The invention is limited only by the spirit and scope of the appended claims. Moreover, these claims may refer to use "first", "second", etc. following with noun or element. Such terms should be understood as a nomenclature and should not be construed as giving the limitation on the number of the elements modified by such nomenclature unless specific number has been given. The abstract of the disclosure is provided to comply with the rules requiring an abstract, which will allow a searcher to quickly ascertain the subject matter of the technical disclosure of any patent issued from this disclosure. It is submitted with the understanding that it will not be used to interpret or limit the scope or meaning of the claims. Any advantages and benefits described may not apply to all embodiments of the invention. It should be appreciated that variations may be made in the embodiments described by persons skilled in the art without departing from the scope of the present invention as defined by the following claims. Moreover, no element and component in the present disclosure is intended to be dedicated to the public regardless of whether the element or component is explicitly implemented in the following claims.

What is claimed is:

1. Medical imaging equipment comprising: a medical equipment, a controller, and a head-mounted display, wherein:
   the medical equipment is configured to investigate a body portion within a patient, and comprise an operational tool with an image capturing device, the image capturing device is configured to capture a first image of the body portion within the patient, and the medical equipment is configured to output a first image signal corresponding to the first image of the body portion, wherein the first image signal has a first resolution;
   the controller is coupled to the medical equipment to receive the first image signal, and converts the first resolution of the first image signal into a second resolution of a second image signal; and
   the head-mounted display is coupled to the controller to display a display image of the second image signal having the second resolution, wherein the head-mounted display has a direction line, and when the head-mounted display faces the body portion, a body portion image of the display image displayed by the head-mounted display, the image capturing device of the operational tool and the body portion of the patient are aligned along to the direction line.

2. The medical imaging equipment according to claim 1, wherein the controller further comprises:
   a scaler board controller adapted to receive the first image signal, convert the first resolution into the second resolution, and output the second image signal having the second resolution; and
   a power supply module coupled to the head-mounted display and adapted to supply power to the head-mounted display.

3. The medical imaging equipment according to claim 1, wherein the controller and the head-mounted display are integral.

4. The medical imaging equipment according to claim 1, wherein the head-mounted display further comprises augmented reality glasses and an optical engine, wherein the second image signal is received by the optical engine and is imaged on the augmented reality glasses.

5. The medical imaging equipment according to claim 4, wherein a transmittance of lenses of the augmented reality glasses is between 60% and 90%.

6. The medical imaging equipment according to claim 4, wherein the head-mounted display further comprises a processor adapted to receive the second image signal and generate a drive signal to drive the optical engine.

7. The medical imaging equipment according to claim 4, wherein the optical engine further comprises a light source and a light valve.

8. The medical imaging equipment according to claim 4, further comprising a detachable goggles disposed on the head-mounted display.

9. The medical imaging equipment according to claim 1, wherein the medical equipment further comprises:
a console having a display, receiving and displaying the first image signal, and transmitting the first image signal to the controller.

10. The medical imaging equipment according to claim 1, wherein the medical equipment outputs the first image signal, and at least one of receiving the first image signal by the controller and receiving the second image signal by the head-mounted display is performed through wireless transmission or wired transmission.

11. The medical imaging equipment according to claim 1, wherein the controller further comprises a clipping part to fix the controller on a user.

12. A medical imaging method adapted for a head-mounted display, medical equipment, and a controller coupled to the head-mounted display and the medical equipment, wherein the medical imaging method comprises:
investigating a body portion within a patient by the medical equipment having an operational tool with an image capturing device;
capturing a first image of the body portion within the patient by the image capturing device;
outputting a first image signal corresponding to the first image of the body portion by the medical equipment, wherein the first image signal has a first resolution;
receiving the first image signal and converting the first resolution of the first image signal into a second resolution of a second image signal by the controller; and
displaying a display image of the second image signal having the second resolution by the head-mounted display, wherein the head-mounted display has a direction line, and when the head-mounted display faces the body portion, a body portion image of the display image displayed by the head-mounted display, the image capturing device of the operational tool and the body portion of the patient are aligned along to the direction line.

13. The medical imaging method according to claim 12, wherein the step of receiving the first image signal and converting the first resolution of the first image signal into the second image signal having the second resolution by the controller further comprises:
receiving the first image signal, converting the first resolution into the second resolution, and outputting the second image signal having the second resolution by a scaler board controller.

14. The medical imaging method according to claim 12, further comprising:
receiving the second image signal and imaging the second image signal on augmented reality glasses by an optical engine.

15. The medical imaging method according to claim 14, wherein a transmittance of lenses of the augmented reality glasses is between 60% and 90%.

16. The medical imaging method according to claim 14, further comprising:
receiving the second image signal and generating a drive signal to drive the optical engine by a processor.

17. The medical imaging method according to claim 14, further comprising:
disposing detachable goggles on the head-mounted display.

18. The medical imaging method according to claim 12, further comprising:
receiving the first image signal, displaying the first image signal on a display of a console, and transmitting the first image signal to the controller by the console.

19. The medical imaging method according to claim 12, wherein the medical equipment outputs the first image signal, and at least one of receiving the first image signal by the controller and receiving the second image signal by the head-mounted display is performed through wireless transmission or wired transmission.

* * * * *